US008921110B1

(12) United States Patent
Jeknic et al.

(10) Patent No.: US 8,921,110 B1
(45) Date of Patent: Dec. 30, 2014

(54) RED IRIS

(71) Applicants: Zoran Jeknic, Corvallis, OR (US); Tony H. H. Chen, Corvallis, OR (US)

(72) Inventors: Zoran Jeknic, Corvallis, OR (US); Tony H. H. Chen, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 15 days.

(21) Appl. No.: 14/023,909

(22) Filed: Sep. 11, 2013

(51) Int. Cl.
*C12N 5/04* (2006.01)
*C12N 5/10* (2006.01)
*C12N 15/82* (2006.01)
*A01G 5/00* (2006.01)

(52) U.S. Cl.
CPC ................ *C12N 15/825* (2013.01); *A01G 5/00* (2013.01)
USPC .......................................... 435/419; 435/468

(58) Field of Classification Search
USPC ........................................................ 800/282
See application file for complete search history.

(56) References Cited

U.S. PATENT DOCUMENTS 5,880,332 A 3/1999 Camara et al.
6,459,017 B1 * 10/2002 Jeknic et al. .................. 800/278
8,143,478 B2 * 3/2012 Umemoto et al. ............ 800/282

OTHER PUBLICATIONS

Meckenstock (Breeding Red Irises: The Carotenoids, Aug. 2005).*
GenBank Accession No. JF304153 (available at http://www.ncbi.nlm.nih.gov/nuccore/JF304153; first published Feb. 7, 2011; accessed Jan. 20, 2014; of record IDS Sep. 11, 2013).*
GenBank Accession No. GU443955 (available at http://www.ncbi.nlm.nih.gov/nuccore/GU443955; first published Jan. 11, 2010; accessed Jan. 20, 2014; of record IDS Sep. 11, 2013).*
Dave'sGarden (online retailer of plants, page for Iris cultivar Harvest of Memories; available at http://davesgarden.com/guides/pf/go/35227; accessed Jan. 28, 2014).*
Martin et al. (Detecting Adaptive Trait Introgression Between Iris fulva and I. brevicaulis in Highly Selective Field Conditions, 172 Genetics, 2481-2489 (2006)).*
Bouvier et al. (1994) Xanthophyll biosynthesis in chromoplasts: isolation and molecular cloning of an enzyme catalyzing the conversion of 5,6-epoxycarotenoid into ketocarotenoid. Plant J. 6:45-54.
Kumagai et al. (1998) Functional integration of non-native carotenoids into chloroplasts by viral-derived expression of capsanthin-capsorubin synthase in Nicotiana benthamiana. Plant J. 14:305-315.
Jeknic et al. (2012) Cloning and functional characterization of a gene for capsanthin-capsorubin synthase from tiger lily (Lilium lancifolium Thunb. 'Splendens'). Plant Cell Physiol. 53:1899-1912.
Jeknic et al. (1999) Genetic transformation of Iris germanica mediated by *Agrobacterium tumefaciens*. J. Amer. Soc. Hort. Sci. 124:575-580.
Voss, D.H. (1992) Relating Colorimeter Measurement of Plant Color to the Royal Horticultural Society Colour Chart. Hort. Science 27(12):1256-1260.
Ohmiya, A. (2013; in press) Qualitative and quantitative control of carotenoid accumulation in flower petals. Sci.Hortic. (2013), http://dx.doi.org/10.1016/j.scienta.2013.06.018.
GenBank accession No. GU443955.1: Llccs genomic sequence; submitted Jan. 11, 2010. Released Oct. 6, 2012.
GenBank accession No. JF304153.1: Llccs mRNA (cDNA) sequence; submitted Feb. 7, 2011. Released Oct. 6, 2012.

* cited by examiner

*Primary Examiner* — Ashwin Mehta
*Assistant Examiner* — Rebecca Coobs
(74) *Attorney, Agent, or Firm* — Dennis A. Bennett

(57) ABSTRACT

Provided are methods for generating iris plants having flowers expressing red, red/orange, or orange/red color, previously non-existing in this plant genus, thereby expanding the color palette of, and generating new and exciting varieties of, ornamental plants. These methods employ capsanthin-capsorubin synthase-encoding nucleotide sequences, and are also applicable to other genera, species, cultivars, and varieties of ornamental plants in which red, red/orange, or orange/red flowers have been desired. The nucleotide sequences and methods disclosed herein can be applied to genera, species, cultivars, and varieties of ornamental plants that produce yellow pigments, or yellow/orange flowers, but no red flowers, to produce novel red-, red/orange, or orange/red-flowering plants. Plants normally producing the yellow pigments antheraxanthin and/or violaxanthin, or yellow or yellow/orange flowers, are preferred for such modification using the presently disclosed, or similar, methods employing capsanthin-capsorubin synthase-encoding nucleotide sequences.

9 Claims, 2 Drawing Sheets

RED IRIS

BACKGROUND

1. Field of the Invention

The present invention relates to the field of transgenic plants. More particularly, the present invention relates to transgenic plants exhibiting modified flower color.

2. Description of Related Art

Horticultural and ornamental markets are driven by innovation in color, shape and other esthetic parameters of the ornamental plants. New colors of roses and carnations, new shapes and colors of flowers find their way to the marketplace every year and the outdated varieties are replaced by new ones. Generation of new and esthetically pleasing varieties is known to be the key force driving the floriculture industry and allowing its growth.

Iris is a winter hardy, herbaceous perennial consisting of approximately 300 species, many of which are popular ornamentals in the temperate regions of the Northern Hemisphere. While being amongst the most horticulturally important species, and having variety of flower colors including yellow, blue, and burgundy, there are currently no iris species with truly red flower color.

Iris flowers have almost no red pigment naturally, and irises currently commercialized as "red" are actually shades of wine, brick, or reddish brown. Two types of pigments contained within iris plant cells, e.g., oil-soluble xanthophylls and carotenoids that produce yellows, pinks, and oranges in flowers, and water-soluble anthocyanins that produce blues and purples, mix in the epidermal layer, resulting in a combination of pigments perceived by the eye as reddish.

*Iris germanica* is one of the most popular iris species. Flower color in *I. germanica* is determined by two distinct biochemical pathways, the carotenoid pathway creates yellow, orange, and pink flowers, while the anthocyanin pathway produces blue and purple flowers. Similarly to the other members of the iris genus, there are no truly red *I. germanica* flowers. Conventional breeding methods have so far failed to generate them due to lack of genes capable of generating truly red pigment within the iris gene pool.

U.S. Pat. No. 5,880,332 discloses the nucleotide sequence of the capsanthin-capsorubin synthase (ccs) gene from pepper (*C. annum*), which catalyzes the biosynthesis of the red carotenoids capsanthin and capsorubin, and does not suggest the newly discovered ccs sequence of lily (*L. lancifolium*) disclosed herein, there being less than 60% sequence homology between the genes. Notably, the lack of significant relationship between the lily and pepper ccs prevented identification of the lily gene using heterologous non-degenerate primers based on the pepper sequence (Jeknic et al. (2012) *Plant & Cell Physiol.* 53(11): 1899-1912). As such, U.S. Pat. No. 5,880,332 does not disclose or suggest *L. lancifolium* ccs, transgenic iris plants containing a ccs gene, or red, or red/orange, irises.

U.S. Pat. No. 6,459,017 discloses methods for transformation and regeneration of transgenic iris plants; however, this patent does not disclose or suggest capsanthin-capsorubin synthase for such transformation, and does not disclose the ccs sequence of lily (*L. lancifolium*), or red, or red/orange, irises.

A truly red bearded iris, like a truly blue rose, has remained an unattained goal for decades despite frequent hybridizing and selection. There are species and selections, most notably based on the beardless rhizomatous Copper iris (*I. fulva*), that have a relatively pure red color. However, introducing this color into a modern bearded iris breed has proven very difficult, and the vast majority of irises are in the purple and blue to blue violet color range, with yellow, pink, orange, and white breeds available.

It would therefore be useful to introduce new genes enabling generation of truly red pigment in the iris genus, beyond what is available in the native iris genome. New varieties of red or red/orange color in iris will produce a long-awaited increase in the assortment and variety of these ornamental plants available to the consumer.

The present invention addresses the need in the art for iris plants with truly red, and red/orange, pigment in their flowers. The methods disclosed herein enable the production of new varieties of red and red/orange colored iris flowers, containing capsanthin and/or capsorubin, satisfying consumer desire for an increase in the assortment and variety of these commercially important ornamental plants.

SUMMARY

Accordingly, the present invention describes materials and methods for generating transgenic iris plants expressing red or red/orange pigment in their flowers, which have not existed prior to this invention, and will enable production of novel red and red/orange iris cultivars and varieties for the horticulture industry.

In one embodiment, the present invention describes the identification of a novel kcapsanthin-capsorubin synthase (ccs) gene from *Lilium lancifolium* (Llccs), suitable for the production of the red pigments capsanthin and capsorubin in plant flowers.

In another embodiment, the present invention discloses expression of the Llccs gene in iris cells and generation of red pigment. While exemplified by the use of Llccs from a lily (*Lilium lancifolium*), the present invention is not limited to a liliaceous-derived Llccs, and is intended to encompass expression of all known, and to be discovered, enzymes with capsanthin-capsorubin synthase activity in iris, as well as the expression of Llccs in any other appropriate transgenic plants, in order to generate desired red or red/orange pigmentation.

In yet another embodiment, the invention describes the identification and functional characterization of the Llccs promoter, suitable for tissue-specific expression of Llccs and other transgenes in iris flowers. Other plant promoters, including flower-specific promoters and constitutive promoters, such as the maize ubiquitin promoter, can be used to express Llccs in transgenic plants.

More particularly, among its many embodiments, the present invention includes:

1. An iris cell transformed with, and which expresses, a heterologous nucleotide sequence encoding a capsanthin-capsorubin synthase (ccs). Such cell can be an *Iris germanica* or *Iris hollandica* cell.
2. The iris cell of 1, wherein said heterologous nucleotide sequence encoding said capsanthin-capsorubin synthase (ccs) is from *Lilium lancifolium, Capsicum annuum, Citrus sinensis, Ricinus communis, Daucus carota*, or *Medicago truncatula.*
3. The iris cell of 1 or 2, wherein said cell is transformed using *Agrobacterium*-mediated or biolistic transformation.
4. The iris cell of any one of 1-3, wherein said heterologous nucleotide sequence encoding said capsanthin-capsorubin synthase (ccs) comprises the nucleotide sequence shown in SEQ ID NO:1.
5. A transgenic iris plant, comprising said cell of any one of 1-4.

6. The transgenic iris plant of 5, wherein said iris plant is cultivar or variety 'Hot Property', 'Dance Man', 'Asian Treasure', 'Strike it Rich', 'Harvest of Memories', 'Early Girl', 'Kissed by the Sun', 'It's Magic', 'Acapulco Gold', 'City of Gold', 'Just a Kiss Away', 'King of Light', 'Dance Till Dawn', or 'Done Me Wrong'.

7. A non-genomic nucleotide sequence encoding *Lilium lancifolium* capsanthin-capsorubin synthase (Llccs).

Non-genomic nucleotide sequences encoding *Lilium lancifolium* capsanthin-capsorubin synthase (Llccs) include, for example, mRNA, and synthetically produced Llccs DNA including, for example, codon-optimized Llccs sequences for efficient expression in different monocots and dicots, etc.

8. The non-genomic nucleotide sequence of 7, comprising the nucleotide sequence shown in SEQ ID NO:1.

9. A plant, cells of which are transformed with, and which express, any of the ccs-encoding nucleotide sequences of 2.

10. The plant of 9, wherein said ccs-encoding nucleotide sequence comprises the nucleotide sequence shown in SEQ ID NO:1.

11. Use of a capsanthin-capsorubin synthase (ccs)-encoding nucleotide sequence to modify the pigment composition in a flower of a plant.

12. The use of 11, wherein said capsanthin-capsorubin synthase (ccs) is from *Lilium lancifolium* or *Capsicum annuum*.

13. The use of 11 or 12, wherein said pigment composition in said flower of said plant comprises yellow or yellow/orange pigments.

The use of any one of 11-13 encompasses application of the nucleotide sequences and methods disclosed herein to genera, species, cultivars, and varieties of ornamental plants that produce yellow or yellow/orange pigments, or yellow or yellow/orange flowers, but no red flowers, to produce novel red-, red/orange-, or orange/red-flowering plants. Plants normally producing the yellow pigments antheraxanthin and/or violaxanthin, or yellow or yellow/orange flowers, are preferred for such modification using the presently disclosed, or similar, methods employing capsanthin-capsorubin synthase coding sequences.

14. An isolated gene promoter sequence comprising the nucleotide sequence shown in SEQ ID NO:2.

15. A plant, other than *Lilium lancifolium*, cells of which comprise SEQ ID NO:2 in their genome.

16. The plant of 15, wherein said SEQ ID NO:2 is operably linked for expression to a nucleotide sequence encoding a peptide, polypeptide, or protein.

17. A plant cell, comprising a heterologous nucleotide sequence encoding *Lilium lancifolium* or *Capsicum annuum* capsanthin-capsorubin synthase (ccs) operably linked to, or co-expressed with, a nucleotide sequence encoding a selection marker or screenable marker functional in a plant. Such plant cell can be other than a *Lilium lancifolium* or *Capsicum annuum* plant cell.

18. A transgenic plant, comprising said cell of 17.

19. An iris plant having one or more flowers exhibiting red, red/orange, or orange/red color.

Such iris plant can be a cultivar or variety of *Iris germanica* or *Iris hollandica*. A flower, or flowers, of such iris plant can have one or more standards, all standards, one or more falls, all falls, a beard, a style crest, a signal, or a combination of any of the foregoing, exhibiting red, red/orange, or orange/red color.

The terms "red", "red/orange", and "orange/red" include all colors falling within the range of from about RHS Colour Chart (2001 Edition) chip 30A to about 56D. Preferred red colors fall within the range of from about RHS Colour Chart chip 36 to about 55; about 40 to about 47; about 42 to about 47; and about 42 to about 45. Preferred orange/red or red/orange colors fall within the range of from about N30 to about N34, preferably from about 32-34, and even more preferably N34. Each of the foregoing ranges includes the end point chips, as well as each of the individual color chips therein, including all the gradients from A through D. All these are contained in Table 1, below, listing RHS Colour Chart chips from 30A through 56D.

20. The iris plant of 19, produced by a method comprising:

a) inserting into the genome of an iris plant cell a recombinant, double-stranded DNA molecule comprising, operably linked for expression:

(i) a promoter sequence that functions in plant cells to cause the transcription of an adjacent coding sequence to RNA;

(ii) a capsanthin-capsorubin synthase coding sequence;

b) obtaining a transformed iris plant cell; and c) regenerating from said transformed iris plant cell a genetically transformed iris plant, cells of which express said capsanthin-capsorubin synthase.

21. The iris plant of 20, wherein said capsanthin-capsorubin synthase is expressed in an amount in cells of said transformed iris plant effective to produce one or more standards, all standards, one or more falls, all falls, a beard, a style crest, a signal, or a combination of any of the foregoing, exhibiting red, red/orange, or orange/red color in one or more flowers.

22. The iris plant of 20 or 21, one or more flowers of which comprises one or more standards, all standards, one or more falls, all falls, a beard, a style crest, a signal, or a combination of any of the foregoing, exhibiting red, red/orange, or orange/red color.

23. The iris plant of any one of 20-22, wherein said capsanthin-capsorubin synthase coding sequence comprises the nucleotide sequence shown in SEQ ID NO:1 or a nucleotide sequence encoding capsanthin-capsorubin synthase of *Capsicum annuum*.

24. The iris plant of any one of 20-23, wherein said promoter is a flower-specific promoter or a constitutive promoter.

The flower-specific promoter can comprise the nucleotide sequence shown in SEQ ID NO:2, a promoter of a phenylpropanoid or flavonoid biosynthetic gene in flowers such as the promoter of a phenylanlanine ammonia lyase (PAL) gene from bean (gPAL2) and the promoters of the chalcone synthase (CHS) and 4-coumarate-CoA-ligase (4-CL) genes; a flower-specific promoter of *Brassica* spp.; a promoter of a chalcone flavanone isomerase gene from *Petunia hybrida*; a *Petunia hybrida* chalcone synthase (chs A) gene; a bean chalcone synthase gene promoter; the region between −1800 bp and −800 bp of petunia EPSPS; or an *Arabidopsis* APETALA3 (AP3) promoter.

The constitutive promoter can comprise the maize ubiquitin promoter, the CaMV 19S promoter, the CaMV35S promoter, the FMV35S promoter, enhanced or duplicate versions of the CaMV35S and FMV35S promoters, the nopaline synthase promoter, the octopine synthase (OCS) promoter, or the rice Act1 promoter.

25. A method of producing an iris plant having one or more flowers comprising one or more standards, all standards, one or more falls, all falls, a beard, a style crest, a signal, or a combination of any of the foregoing, exhibiting red, red/orange, or orange/red color, comprising:

a) inserting into the genome of an iris plant cell a recombinant, double-stranded DNA molecule comprising, operably linked for expression:
(i) a promoter sequence that functions in plant cells to cause the transcription of an adjacent coding sequence to RNA;
(ii) a capsanthin-capsorubin synthase coding sequence;
b) obtaining a transformed iris plant cell; and
c) regenerating from said transformed iris plant cell a genetically transformed iris plant, cells of which express said capsanthin-capsorubin synthase.

Such iris plant can be a cultivar or variety of *Iris germanica* or *Iris hollandica* including, but not limited to, 'Hot Property', 'Dance Man', 'Asian Treasure', 'Strike it Rich', 'Harvest of Memories', 'Early Girl', 'Kissed by the Sun', 'It's Magic', 'Acapulco Gold', 'City of Gold', 'Just a Kiss Away', 'King of Light', 'Dance Till Dawn', or 'Done Me Wrong'.

26. The method of 25, wherein said capsanthin-capsorubin synthase is expressed in an amount in cells of said transformed iris plant effective to produce one or more standards, all standards, one or more falls, all falls, a beard, a style crest, a signal, or a combination of any of the foregoing, exhibiting red, red/orange, or orange/red color in one or more flowers.

27. The method of 25 or 26, wherein said iris plant has one or more flowers that comprises one or more standards, all standards, one or more falls, all falls, a beard, a style crest, a signal, or a combination of any of the foregoing, exhibiting red, red/orange, or orange/red color.

28. The method of any one of 25-27, wherein said capsanthin-capsorubin synthase coding sequence comprises the nucleotide sequence shown in SEQ ID NO:1 or a nucleotide sequence encoding capsanthin-capsorubin synthase of *Capsicum annuum.*

29. The method of any one of 25-28, wherein said promoter is a flower-specific promoter.

The flower-specific promoter can comprise the nucleotide sequence shown in SEQ ID NO:2, a promoter of a phenylpropanoid or flavonoid biosynthetic gene in flowers such as the promoter of a phenylanlanine ammonia lyase (PAL) gene from bean (gPAL2) and the promoters of the chalcone synthase (CHS) and 4-coumarate-CoA-ligase (4-CL) genes; a flower-specific promoter of *Brassica* spp.; a promoter of a chalcone flavanone isomerase gene from *Petunia hybrida*; a *Petunia hybrida* chalcone synthase (chsA) gene; a bean chalcone synthase gene promoter; the region between −1800 bp and −800 bp of petunia EPSPS; or an *Arabidopsis* APETALA3 (AP3) promoter.

The constitutive promoter can comprise the maize ubiquitin promoter, the CaMV 19S promoter, the CaMV35S promoter, the FMV35S promoter, enhanced or duplicate versions of the CaMV35S and FMV35S promoters, the nopaline synthase promoter, the octopine synthase (OCS) promoter, or the rice Act1 promoter.

30. An iris plant produced by the method of any one of 25-29.

31. A recombinant, double-stranded DNA molecule comprising, operatively linked for expression:
a) a promoter that functions in plant cells to cause transcription of an adjacent coding sequence to RNA; and
b) a nucleotide sequence encoding a capsanthin-capsorubin synthase selected from the group consisting of the nucleotide sequences recited in 2.

32. The recombinant, double-stranded DNA molecule of 31, wherein said promoter is a flower-specific promoter or a constitutive promoter.

The flower-specific promoter can comprise the nucleotide sequence shown in SEQ ID NO:2, a promoter of a phenylpropanoid or flavonoid biosynthetic gene in flowers such as the promoter of a phenylanlanine ammonia lyase (PAL) gene from bean (gPAL2) and the promoters of the chalcone synthase (CHS) and 4-coumarate-CoA-ligase (4-CL) genes; a flower-specific promoter of *Brassica* spp.; a promoter of a chalcone flavanone isomerase gene from *Petunia hybrida*; a *Petunia hybrida* chalcone synthase (chsA) gene; a bean chalcone synthase gene promoter; the region between −1800 bp and −800 bp of petunia EPSPS; or an *Arabidopsis* APETALA3 (AP3) promoter.

The constitutive promoter can comprise the maize ubiquitin promoter, the CaMV 19S promoter, the CaMV35S promoter, the FMV35S promoter, enhanced or duplicate versions of the CaMV35S and FMV35S promoters, the nopaline synthase promoter, the octopine synthase (OCS) promoter, or the rice Act1 promoter.

33. The recombinant, double-stranded DNA molecule of 31 or 32, which is codon-optimized for expression in a monocot or a dicot of interest.

34. The recombinant, double-stranded DNA molecule of 33, wherein said monocot is an iris. Such iris can be *Iris germanica* or *Iris hollandica.*

35. An expression construct, comprising said recombinant, double-stranded DNA molecule of any one of 31-34.

36. A part of said plant of any one of 5-6, 9-10, 15-16, 18-24, or 30.

37. The part of 36, which is selected from the group consisting of a protoplast, a cell, a tissue, an organ, a cutting, and an explant.

38. The plant part of 36 or 37, which is selected from the group consisting of an inflorescence, a flower, one or more flowers with stem attached, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a bulb, a tuber, a stolon, a corm, a bulb, an offset, a cell of said plant in culture, a tissue of said plant in culture, an organ of said plant in culture, and a callus.

39. Progeny of said plant of any one of 5-6, 9-10, 15-16, 18-24, or 30.

40. The progeny of 39, which is produced sexually or asexually.

41. A seed, tuber, or rhizome of said plant of any one of 5-6, 9-10, 15-16, 18-24, or 30.

42. A flower arrangement or bouquet, comprising one or more flowers, or one or more flowers with stem attached, of said plant of any one of 5-6, 9-10, 15-16, 18-24, or 30.

43. A method of making a flower arrangement or bouquet, comprising including in a flower arrangement or bouquet one or more flowers, or one or more flowers with stem attached, of said plant of any one of 5-6, 9-10, 15-16, 18-24, or 30.

Also encompassed by the present invention is the application of the methods of 25-29, and the use of the recombinant, double-stranded DNA molecules and expression constructs of 31-34 and 35, respectively, to modify the pigment composition of flowers of other genera, species, cultivars, and varieties of ornamental plants beyond irises in which red, red/orange, or orange/red flowers have been desired, but which are not currently available and/or have proven difficult to produce. Thus, the present invention encompasses application of the nucleotide sequences and methods disclosed herein to genera, species, cultivars, and varieties of ornamentals that produce yellow pigments, or yellow or yellow/orange flowers, but no red, red/orange, or orange/red flowers, to produce novel red-, red/orange-, or orange/red-flowering plants. Plants that normally produce yellow or yellow/orange flowers, especially those containing the yellow pigments antheraxanthin and/or violaxanthin, are preferred for such modification using the presently disclosed, or similar, methods employing ccs-encoding nucleotide sequences.

Further scope of the applicability of the present invention will become apparent from the detailed description and drawing(s) provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other aspects, features, and advantages of the present invention will be better understood from the following detailed description taken in conjunction with the accompanying drawing(s), all of which are given by way of illustration only, and are not limitative of the present invention, in which.

DETAILED DESCRIPTION

Figure 1:
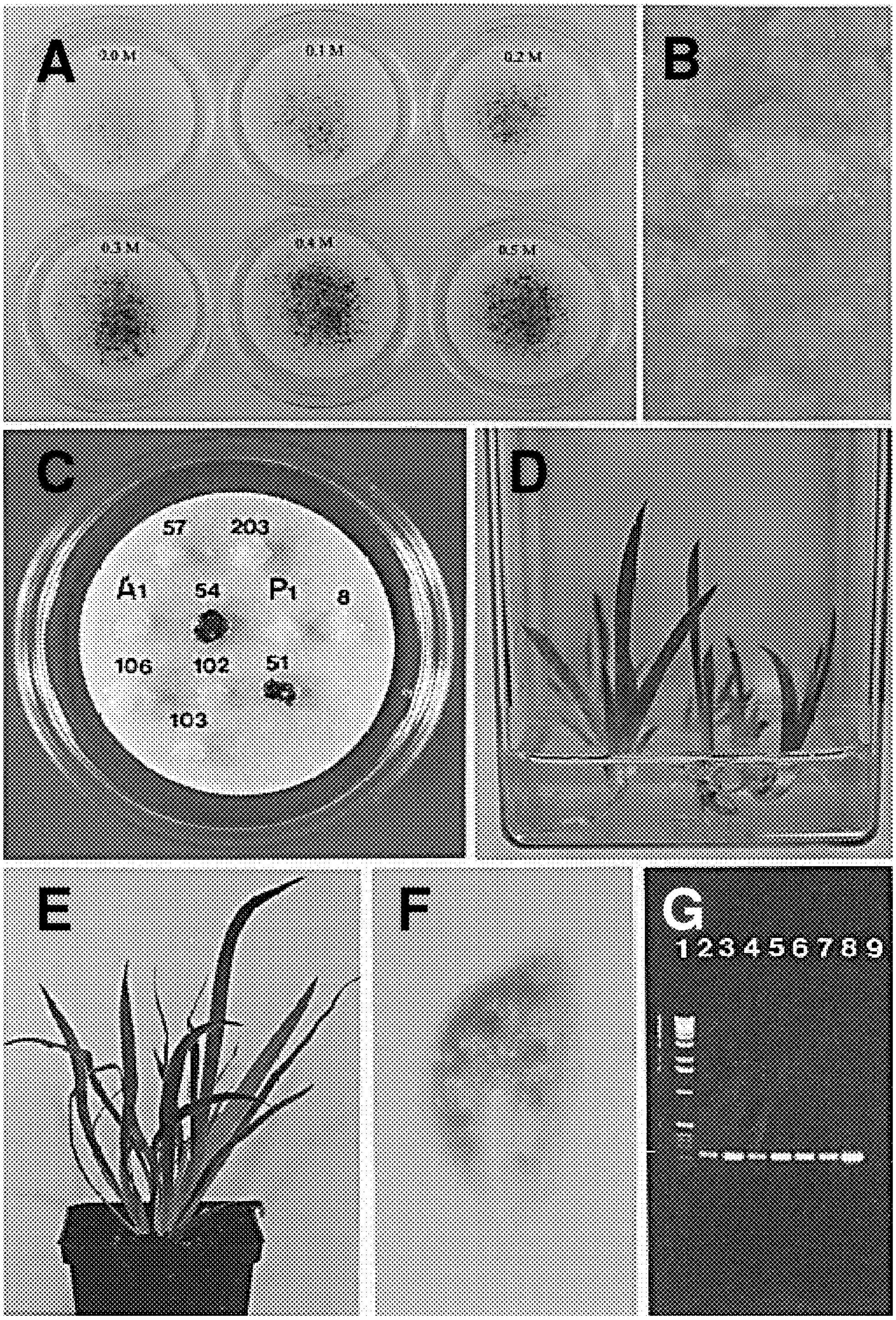
FIG. 1. Steps in biolistic transformation and regeneration of transgenic his plants. (A) Effect of increasing concentrations of osmoticum (equimolar concentration of mannitol and sorbitol) on transient expression of the GUS gene 48 hours after transformation. (B) Several cell clumps that proliferated on selection medium (MS-C containing 10 mg L-1 Basta) about 2 weeks later. (C) Stable transformation of callus lines #54 and #51 confirmed by GUS staining several weeks later. (D) Regenerated transgenic plants from callus #54 on MS-R medium. (E) Transgenic plant derived about 4 weeks after transfer to soil. (F) Staining of the leaf section for expression of the GUS gene. (G) Separation of a 250 bp fragment from the coding region of uidA (GUS) gene, amplified using PCR from genomic DNA of several independent transgenic plants, and separated by agarose electrophoresis. Key: 1 100 bp ladder, 2-7 transgenic plants, 8 positive control (plasmid), 9 negative control (non-transformed plant).

The following detailed description is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The following definitions are provided to aid the reader in understanding the various aspects of the present invention. Unless defined otherwise, all technical and scientific terms used herein have the same meaning as commonly understood by those of ordinary skill in the art to which the invention pertains. Provision, or lack of the provision, of a definition for a particular term or phrase is not meant to signify any particular importance, or lack thereof. Rather, and unless otherwise noted, terms are to be understood according to conventional usage by those of ordinary skill in the art.

The contents of each of the documents cited herein are herein incorporated by reference in their entirety.

DEFINITIONS

Unless otherwise noted, technical terms are used according to conventional usage. Definitions of common terms in molecular biology can be found, for example, in J. Kendrew, Ed., *The Encyclopedia of Molecular Biology*, Blackwell Science Ltd., Oxford, 1995; Lewin, *Genes IX*, Oxford University Press and Cell Press, New York, 2006; Buchanan, et al., *Biochemistry and Molecular Biology of Plants*, Courier Companies, USA, 2000; Alberts, et al., *Molecular Biology of the Cell* ($5^{th}$ edition), 2008; and Lodish et al., *Molecular Cell Biology* ($7^{th}$ edition), W.H. Freeman Company, New York, 2013. The nomenclature for DNA bases as set forth in 37 CFR §1.822 is used.

The singular terms "a", "an", and "the" include plural referents unless the context in which they appear clearly indicates otherwise.

About: The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ±a range of up to 20%, up to 15%, up to 10%, up to 5%, or up to 4%, 3%, 2%, or 1% compared to the specifically recited value.

If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.).

Cultivars and varieties: These terms encompass all cultivars, plants selected for desirable characteristics that can be maintained by propagation, and cultivars recognized as varieties, belonging to the iris genus.

Flower: A typical flower comprises a pedicel, sepals, petals, stamens, and one or more pistils, which are composed of two or more hollow subunit structures called carpals fused together. A stamen comprises an anther, pollen, and filament. A carpel comprises a stigma, style and ovary. An ovary comprises an ovule, embryo sac, and egg cell. A "flower cell" is a cell from any one of these structures. In general, flower-specific promoters include promoters that direct gene expression in any of the above tissues or cell types.

Characteristic flower parts of irises are discussed below in the section entitled "Standards, Falls, Beards, Style Crests, and Signals".

Flower-specific promoters and flower-preferred promoters: These terms can be used interchangeably, and refer to promoters active in flowers, with promoter activity being significantly higher in flower tissue versus non-flower tissue.

Such promoters preferentially initiate transcription in flower cells compared to cells in other parts of a plant. Preferably, the promoter activity in terms of expression levels of an operably linked sequence is more than two-, three-, four- or five-fold, or more than ten-fold, higher in flower cells and tissues than in non-flower cells and tissues. Thus, such promoters can be active in flowers, while being essentially inactive, or active at very low levels, in non-flower tissues and cells.

Examples of flower-specific promoters include those of phenylpropanoid and flavonoid biosynthetic genes in flowers, such as the promoter of a phenylanlanine ammonia lyase (PAL) gene from bean (gPAL2) and the promoters of the chalcone synthase (CHS) and 4-coumarate-CoA-ligase (4-CL) genes (discussed in Sablowski et al. (1994) *EMBO Journal* 13(1):128-137; four flower-specific promoters of *Brassica* spp. (Geng et al. (2009) *African Journal of Biotechnology* 8(20):5193-5200); promoters of chalcone flavanone isomerase genes from *Petunia hybrida* (van Tunen et al. (1988) *EMBO Journal* 7:1257-1263); a *Petunia hybrida* chalcone synthase (chsA) gene (van der Meer et al. (1990) *Plant Mol. Biol.* 15:95-109; a bean chalcone synthase gene promoter (Faktor et al. (1996) *Plant Mol. Biol.* 32:849-859); the region between −1800 bp and −800 bp of petunia EPSPS (Benfey et al. (1989) *Science* 244:174-181); and an *Arabidopsis* APETALA3 (AP3) promoter (Hill et al. (1998) *Development* 125:1711-1721; Fan et al. (2012) *Plant Gene and Trait* 3(5):22-27 (doi: 10.5376/pgt.2012.03.0005)).

Constitutive promoters: While flower-specific and flower-preferred promoters are useful for producing plants with flowers exhibiting red, red/orange, or orange/red coloration, constitutive promoters can also be employed in the methods of the present invention to achieve the same effect.

Constitutive promoters typically provide for the constant and substantially uniform production of proteins in all tissues. For example, the promoter can be a viral promoter such as a CaMV35S or FMV35S promoter. The CaMV35S and FMV35S promoters are active in a variety of transformed plant tissues and most plant organs (e.g., callus, leaf, seed, and root). Enhanced or duplicate versions of the CaMV35S and FMV35S promoters can be particularly useful in the practice of the present invention. Note U.S. Pat. Nos. 5,378,619 and 5,463,175, and PCT International Publication WO 84/02913, each of which is incorporated herein by reference in its entirety. Other useful constitutive promoters include the nopaline synthase (NOS) and octopine synthase (OCS) promoters (which are carried on tumor-inducing plasmids of *A. tumefaciens*), the cauliflower mosaic virus (CaMV) 19S promoter, the maize ubiquitin promoter, and the rice Act1 promoter.

The rationale for using constitutive promoters in the presently disclosed methods is that the required precursor pigments antheraxanthin and/or violaxanthin for capsanthin and capsorubin biosynthesis, respectively, are not present in significant amounts in plant tissues other than flowers. Thus, the activity of such promoters will not be evident in these other tissues. The same reasoning applies to flower-specific promoters with low specificity that also exhibit some level of activity in non-flower cells and tissues. Accordingly, both of these types of promoters will be useful in the present methods.

Heterologous: The term "heterologous" refers to a nucleic acid fragment or protein that is foreign to its surroundings. In the context of a nucleic acid fragment, this is typically accomplished by introducing such fragment, derived from one source, into a different host. Heterologous nucleic acid fragments, such as coding sequences that have been inserted into a host organism, are not normally found in the genetic complement of the host organism. As used herein, the term "heterologous" also refers to a nucleic acid fragment derived from the same organism, but which is located in a different, e.g., non-native, location within the genome of this organism. Thus, the organism can have more than the usual number of copy(ies) of such fragment located in its(their) normal position within the genome and in addition, in the case of plant cells, within different genomes within a cell, for example in the nuclear genome and within a plastid or mitochondrial genome as well. A nucleic acid fragment that is heterologous with respect to an organism into which it has been inserted or transferred is sometimes referred to as a "transgene."

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter effects the transcription or expression of the coding sequence.

Plant: The term "plant" encompasses transformed plants, progeny of such transformed plants, and parts of plants, including reproductive units of a plant, fruit, flowers, seeds, etc. The transformation methods and compositions of the present invention are particularly useful for transformation of monocots, including ornamental monocots such as members of the family Iridaceae, especially species, varieties, and cultivars of the genus *Iris*. Other species of monocotyledonous and dicotyledonous plants can also be transformed using the disclosed methods. In such other cases, the nucleotide sequences disclosed herein may have to be codon-optimized for maximum activity using methods well known in the art.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

"Red" and "Red/Orange" or "Orange/Red": As used herein, the primary reference standard for defining these flower colors is the Royal Horticultural Society (RHS) Colour Chart, 2001 Edition, which is used as the standard reference for plant color identification by the Royal Horticultural Society, gardeners, and as noted below, the U.S. Patent and Trademark Office. The color chart is arrayed in four color fans containing 808 color chips on 202 leaves. A new edition was published in 2007. As of the filing date of this application, a search of the United States Patent and Trademark Office website for "red" and "red orange" or "orange red" revealed over 3,900 plant patents, and approximately 500 utility patents, referring to RHS color chart chip numbers in their specifications.

Desirable shades of the red in *I. germanica* and the other iris species disclosed herein include, for example, those close to vermilion (a brilliant red); scarlet (a bright red color with a hue that is somewhat toward orange and which is redder than vermilion); crimson (a strong, bright, deep red color); carmine; and orange red.

With reference to the RHS Colour Chart, 2001 Edition, for the purposes of the present invention, the terms "red" and "orange/red" or "red/orange" include colors falling within the range of from about RHS color chart chip 30A to about 56D. Preferred red colors fall within the range of from about RHS color chart chip 36 to about 55; about 40 to about 47; about 42 to about 47; and about 42 to about 45. Preferred orange/red or red/orange colors fall within the range of from about N30 to about N34, preferably from about 32-34, and even more preferably N34. Each of the foregoing ranges (and individual color chips) includes the end points, as well as each of the individual color chips therein, including all the gradients from A through D, where present in the color chart.

Table 1 lists the RHS Colour Chart chips relied upon herein:

TABLE 1

| RHS Colour Chart Chips, 2001 Edition |
|---|
| 30A |
| 30B |
| 30C |
| 30D |
| N30A |
| N30B |
| N30C |
| N30D |
| 31A |
| 31B |
| 31C |
| 31D |
| 32A |
| 32B |
| 32C |
| 32D |
| 33A |
| 33B |
| 33C |
| 33D |
| 34A |
| 34B |
| 34C |
| 34D |
| N34A |
| N34B |
| N34C |
| N34D |
| 35A |
| 35B |
| 35C |
| 35D |
| 36A |
| 36B |
| 36C |
| 36D |
| 37A |
| 37B |
| 37C |
| 37D |
| 38A |
| 38B |
| 38C |
| 38D |
| 39A |
| 39B |
| 39C |
| 39D |
| 40A |
| 40B |
| 40C |
| 40D |
| 41A |
| 41B |
| 41C |
| 41D |
| 42A |
| 42B |
| 42C |
| 42D |
| 43A |
| 43B |
| 43C |
| 43D |
| 44A |
| 44B |
| 44C |
| 44D |
| 45A |
| 45B |
| 45C |
| 45D |
| 46A |
| 46B |
| 46C |
| 46D |
| 47A |
| 47B |
| 47C |
| 47D |
| 48A |
| 48B |
| 48C |
| 48D |
| 49A |
| 49B |
| 49C |
| 49D |
| 50A |
| 50B |
| 50C |
| 50D |
| 51A |
| 51B |
| 51C |
| 51D |
| 52A |
| 52B |
| 52C |
| 52D |
| 53A |
| 53B |
| 53C |
| 53D |
| 54A |
| 54B |
| 54C |
| 54D |
| 55A |
| 55B |
| 55C |
| 55D |
| 56A |
| 56B |
| 56C |
| 56D |

Voss ((1992) *Hort. Science* 27(12):1256-1260) describes an instrumental colorimetric method for converting RHS color chart colors into quantitative criteria based on the CIELAB system, which established a system of numerical coordinates to locate individual colors in a "color solid" based on uniform visual color spacing, standardizing colorimetric practice for the scientifically and industrially important problems of color discrimination and color spacing. In the color solid, the axes are designated as L*, a*, and b* (pronounced "L-star," etc.). This method substitutes instrumental measurement for visual color evaluation, providing accurate color notation and avoiding possible pitfalls associated with visual evaluation, and correlates the measurements with the RHS Colour Chart widely used by botanists and horticulturalists.

The present invention therefore also incorporates the CIELAB values corresponding to the RHS Colour Chart chips disclosed herein, obtained via the method described by Voss.

By way of example, Table 2 in Voss discloses CIE coordinates for a number of RHS color chips from the 1986 edition of the RHS Colour Chart.

Standards, Falls, Beards, Style Crests, and Signals: his flowers are fan-shaped, and contain one or more symmetrical six-lobed flowers that grow on a pedicel, or lack a footstalk. The three sepals, which either spread or droop downwards, are referred to as "falls". The three flower petals that stand upright, partly behind the sepal bases, are called "standards". In *Iris germanica*, the "beard" is the tuft of thick bushy hairs on the upper part of each of the three falls. On beardless irises, there is often a "signal" consisting of a bright contrasting spot of a different color that replaces the beard. The "style crest" is the flared end of the style arm, usually split into two projections and often serrated.

Transformed; Transgenic: A cell, tissue, organ, or organism into which a foreign nucleic acid, such as a recombinant nucleic acid molecule (e.g., a recombinant vector), has been introduced is considered "transformed" or "transgenic," as are progeny thereof in which the foreign nucleic acid is present. As used herein, the term transformation encompasses all techniques by which a nucleic acid molecule (e.g., a recombinant nucleic acid molecule) can be introduced into such a cell, including transfection with viral vectors, transformation with plasmid vectors, and introduction of naked DNA, e.g., via particle gun bombardment and other methods, or *Agrobacterium*-mediated transformation.

Red, Red/Orange Irises

Irises are one of the most horticulturally important plant species. In *Iris germanica*, flower color is determined by two distinct biochemical pathways. The carotenoid pathway creates yellow, orange, and pink flowers, while the anthocyanin pathway produces blue and purple flowers. In nature, there are no truly red iris flowers, and conventional breeding methods have so far failed to generate them. Genetic engineering provides a means of introducing new traits by expanding the gene pool beyond what is available in the iris genome.

In liliaceous plants, a single gene is responsible for the red and orange flower color, causing accumulation of two red pigments in its flowers, i.e., capsanthin and capsorubin. This enzyme, known as capsanthin-capsorubin synthase (Llccs), catalyzes the conversion of two yellow pigments, antheraxanthin and violaxanthin, into capsanthin and capsorubin, respectively. Prior to the present invention, it was not known if ccs-type enzymes are capable of generating red or red/orange pigments in iris. The inventors decided to determine if Llccs can be used to produce red or red/orange pigment in yellow pigment-producing iris plants.

Prior to the present invention, it was not possible to predict with certainty if a specific plant species, naturally containing the appropriate yellow carotenoid precursor pigments, would produce the noted red pigments upon expression of a transgene encoding for the Llccs enzyme due to, for example, unpredictability of levels of precursor pigments and levels of transformed pigments produced, ability of the Llccs enzyme to properly function, and its stability, in a species-specific cellular environment, etc. They therefore designed an experimental approach to assess whether expression of an Llccs-type enzyme will result in production of red or red/orange pigmented iris flowers.

Currently, only the ccs from bell pepper *Capsicum annuum* (*C. annuum*, e.g. GenBank X76165.1) has been characterized. Several putative homologues of ccs genes from other species have been proposed, including *Citrus sinensis* (GenBank accession No. AF169241.1), *Ricinus communis* (GenBank accession No. XP_002523837.1), *Daucus carota* (GenBank accession Nos. ABB52072.1 and AF208530.1) and *Medicago truncatula* (GenBank accession No. AES67093.1). At the present time, these genes are known only through their sequence annotations, and none of these enzymes has been shown to have ccs-like activity, or to produce and/or result in accumulation of capsanthin and capsorubin. However, they are mentioned here as they may be useful in the present invention.

In the present invention, the inventors identified a novel ccs gene from a lily species, *Lilium lancifolium* (SEQ ID NO:1), designated as Llccs. Notably, initial attempts to identify the gene using heterologous non-degenerate primers based on the sequence of the homologous ccs gene from *C. annuum* failed. A different and novel approach to identity the *L. lancifolium* Llccs gene was utilized and demonstrated to be successful. Further, the inventors have identified the promoter of the Llccs gene (SEQ ID NO:2), and have shown its utility for expression of transgenes in monocots and in flowers Importantly, other promoters active in plant cells (e.g., maize ubiquitin promoter, etc.) can be used to express Llccs in transgenic plants (e.g., iris), and the present invention encompasses all these alternatives.

Promoters expressible in plant cells, including constitutive promoters such as the maize ubiqutin promoter, and flower-specific promoters, are well known in the art.

The inventors previously developed protocols for the transformation and regeneration of transgenic iris plants (U.S. Pat. No. 6,459,017), enabling introduction of novel transgenes and traits into irises. The inventors have utilized this technology to introduce the *L. lancifolium* Llccs gene into iris cells, and thus demonstrate production of red or red/orange pigment in iris tissues. Iris cells harboring the Llccs transgene changed color from their normal yellow into orange/red. Analysis of carotenoid extracts from the orange/red callus revealed that the new pigmentation was due to the accumulation of capsanthin and capsorubin, indicating that the Llccs gene was functioning correctly in transgenic iris (Jeknic et al. (2012) *Plant & Cell Physiol.* 53(11): 1899-1912).

Useful Varieties and Cultivars

Without negating the fact that the current invention encompasses all plants within the family Iridaceae, especially the genus *Iris*, certain cultivars and varieties are preferred for use with this invention. In particular, cultivars and varieties producing yellow pigments, e.g., antheraxanthin and violaxanthin, capable of being transformed to red or red/orange derivatives by the action of a capsanthin-capsorubin synthase, are suitable for generation of flowers exhibiting the red or red/orange pigments. Any yellow- or yellow/orange-flowering iris species, cultivar, or variety, particularly those containing antheraxanthin and/or violaxanthin, are suitable for transformation with the Llccs or any other ccs gene, cDNA, synthetic DNA (such as codon-optimized DNA), etc., encoding a protein exhibiting capsanthin-capsorubin synthase activity. Useful iris plants include, for example, yellow-flowering *Iris germanica* and *Iris hollandica* that produce antheraxanthin and/or violaxanthin in their flowers.

Species, cultivars, and varieties that contain higher amounts of the precursor carotenoids antheraxanthin and/or violaxanthin in flower cells are more likely to produce deeper shades of red color. Furthermore, depending upon the naturally occurring absolute levels of these carotenoid precursors in flower cells; their ratio relative to one another; their ratios to other naturally occurring pigments within cells of flowers in a selected species, cultivar, or variety; the strength and tissue/cell specificity of the promoter used for ccs expression; the location of cells within various flower parts in which the heterologous capsanthin-capsorubin synthase enzyme is expressed; the level of enzymatic activity of expressed heterologous capsanthin-capsorubin synthase in flower cells of a particular species, cultivar, or variety; etc., one can expect to obtain transgenic plants whose flowers exhibit a range of colors within the red to red/orange or orange/red spectrum exemplified by the RHS Colour Chart chips listed in Table 1, and in different flower parts, such as standards, falls, or both, and possibly in other flower parts as well. Thus, the present invention enables the creation of a wealth of new diversity in both color and color patterning in irises and other plant species amenable to the methods disclosed herein.

Most preferred for use in the present invention are bearded, rhizomatous irises, especially *Iris germanica* and its numerous cultivars and varieties, especially those whose flower cells contain antheraxanthin and/or violaxanthin. Specific cultivars and varieties include, but are not limited to, 'Hot Property', 'Dance Man', 'Asian Treasure', 'Strike it Rich', 'Harvest of Memories', 'Early Girl', 'Kissed by the Sun', 'It's Magic', 'Acapulco Gold', 'City of Gold', 'Just a Kiss Away', 'King of Light', 'Dance Till Dawn', and 'Done Me Wrong'.

Also preferred are cultivars and varieties of *Iris hollandica* ("Dutch" iris, cut iris), especially those having yellow flowers, cells of which contain antherxanthin and/or violaxanthin.

The same considerations apply to other genera, species, cultivars, and varieties of ornamental plants in which red or red/orange flowers have been desired, but which are not currently available and/or have proven difficult to produce. Thus, the present invention encompasses application of the nucleotide sequences and methods disclosed herein to genera, species, cultivars, and varieties of ornamental plants that produce yellow pigments, or yellow or yellow/orange flowers, but no red flowers, to produce novel red or red/orange-flowering plants. Plants normally producing the yellow pigments antheraxanthin and/or violaxanthin, or yellow or yellow/orange flowers, are preferred for such modification using the presently disclosed, or similar, methods employing ccs genes, codon-optimized coding sequences, cDNAs, etc.

Variant Nucleotide Sequences Useful in the Present Invention

The present invention further encompasses variants of the nucleotide sequences described herein. Variants may occur naturally, such as a natural allelic variant. Other variants include those produced by nucleotide substitutions, deletions, or additions. The substitutions, deletions, or additions may involve one or more nucleotides. These variants may be altered in coding regions, non-coding regions, or both. Alterations in the coding regions may produce conservative or non-conservative amino acid substitutions, or amino acid deletions or additions. Preferably, the variant is a silent substitution, addition, or deletion, which does not alter the properties and activities of the polypeptide encoded by the nucleotide sequence described herein. Conservative substitutions are also preferred.

A variant of a sequence disclosed herein encompassed by the present invention comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to a sequence disclosed herein. For example, a variant nucleotide sequence that is at least 95% identical to a disclosed nucleotide sequence is identical to the latter sequence, except that the variant nucleotide sequence may include up to five point mutations per each 100 nucleotides of the reference nucleotide sequence described herein. Variant Llccs enzymes encompassed by the present invention preferably exhibit about ±25% of the enzymatic activity exhibited by the Llccs enzyme encoded by the nucleotide sequence disclosed herein (SEQ ID NO:1).

As used herein, the phrase "sequence identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., *SIAM J. Applied Math.,* 48: 1073 (1988). Methods to determine identity are designed to give the largest match between the sequences tested. Moreover, methods to determine identity are codified in publicly available computer programs.

Optimal alignment of sequences for comparison can be conducted, for example, by the local homology algorithm of Smith & Waterman, by the homology alignment algorithms, by the search for similarity method or, by computerized implementations of these algorithms (GAP, BESTFIT, PASTA, and TFASTA in the GCG Wisconsin Package, available from Accelrys, Inc., San Diego, Calif., United States of America), or by visual inspection. See generally, (Altschul, S. F. et al., *J. Mol. Biol.* 215: 403-410 (1990) and Altschul et al. *Nucl. Acids Res.* 25: 3389-3402 (1997)).

One example of an algorithm that is suitable for determining percent sequence identity and sequence similarity is the BLAST algorithm, which is described in (Altschul, S., et al., NCBI NLM NIH Bethesda, Md. 20894; & Altschul, S., et al., *J. Mol. Biol.* 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold.

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always; 0) and N (penalty score for mismatching residues; always; 0). For amino acid sequences, a scoring matrix is used to calculate the cumulative score. Extension of the word hits in each direction are halted when: the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in one embodiment less than about 0.1, in another embodiment less than about 0.01, and in still another embodiment less than about 0.001.

Those of ordinary skill in the art will also recognize that variant sequences encompassed by the present invention include sequences that differ from those disclosed herein due to the well known degeneracy of the genetic code.

It should be noted that the nucleotide and amino acid sequences useful in the methods and plants of the present invention can comprise, consist essentially of, or consist of, any of the sequences disclosed herein.

Recombinant Methods

Practice of the present invention employs, unless otherwise indicated, conventional techniques of molecular biology, recombinant DNA technology, microbiology, chemistry, etc., which are well known in the art and within the capabilities of those of ordinary skill in the art. Such techniques include the following non-limiting examples: preparation of cellular, plasmid, and bacteriophage DNA; manipulation of purified DNA using nucleases, ligases, polymerases, and DNA-modifying enzymes; introduction of DNA into living cells; cloning vectors for various organisms; PCR; chromatographic methods; etc.

Such methods are well known in the art and are described, for example, in Green and Sambrook (2012) *Molecular Cloning: A Laboratory Manual*, Fourth Edition, Cold Spring Harbor Laboratory Press; Ausubel et al. (2003 and periodic supplements) *Current Protocols in Molecular Biology*, John Wiley & Sons, New York, N.Y.; and *Lab Ref: A Handbook of Recipes, Reagents, and Other Reference Tools for Use at the Bench*, Edited by Jane Roskams and Linda Rodgers (2002) Cold Spring Harbor Laboratory Press. The entire contents of each of these texts is herein incorporated by reference.

Jeknic et al. (2012) *Plant & Cell Physiol.* 53(11): 1899-1912 and U.S. Pat. No. 6,459,017, both by the present inventors, disclose details of recombinant methods, transformation, and regeneration protocols applicable to iris species. The latter discloses that the transformation and regeneration methods disclosed therein are applicable to any species of the genus *Iris*, including *Iris germanica, I. hollandica, I. pallida, I. setosa, I. lavigata*, and *I. pumila*, and that the described methods are effective independent of the ploidy of the *Iris*, and therefore find equal application in, for instance, diploid, tetraploid, and hexaploid varieties, as well as variants that are aneuploid for one or more chromosomes. The contents of each of these two references are incorporated by reference herein in their entirety.

The following examples are provided to illustrate various aspects of the present invention, and should not be construed as limiting the invention only to these particularly disclosed embodiments. The materials and methods employed in the examples below are for illustrative purposes, and are not intended to limit the practice of the present invention thereto. Any materials and methods similar or equivalent to those described herein as would be apparent to one of ordinary skill in the art can be used in the practice or testing of the present invention.

Example 1

Molecular Cloning and Sequence Analysis of the Llccs Gene

The strategy for cloning the Llccs gene from *Lilium lancifolium* was based on the fact that lycopene cyclase (LCY), neoxanthin synthase (NSY), and CCS have strong sequence homology and similar putative catalytic mechanisms.

We first decided to try to obtain a partial cDNA sequence of the gene for lycopene β-cyclase (LllcyB) that was located between two adjacent regions that are conserved in both the lcyB gene and the ccs gene from pepper, and then to use the resultant sequence information to synthesize a number of primers for 3' rapid amplification of cDNA ends (RACE). We postulated that this approach (3'RACE) would allow us to clone the 3'-proximal end of LllcyB. However, because of the presumed strong similarity of the LllcyB to Llccs and the matching codon usage, we hoped that some of the primers might preferentially amplify Llccs instead of LllcyB or might, at least, generate mixed PCRs with amplicons of both genes. Therefore, we decided to clone both LllcyB and Llccs candidate genes and then to determine which one was the true Llccs gene by sequence analysis and functional characterization in a suitable test system.

A pair of heterologous, non-degenerate primers, forward (Cs-F, 5'-TGGAGTTTGGGTTGATGAGT-3' (SEQ ID NO:3) and reverse (Cs-R, 5'-TGGGAATCTCTCCAATCCAT-3' (SEQ ID NO:4), amplified a DNA fragment (~400 bp) that encoded a deduced amino acid sequence with strong similarity to that of LCYB. We designed a number of forward primers that were based on this newly cloned sequence and used them in combination with the 3'-outer primer from the RACE kit (FirstChoice RLM-RACE Kit, Ambion, according to the manufacturer's instructions) to try and clone the 3'-proximal ends of both LllcyB and Llccs by 3'RACE. Several of the products of PCR that we obtained were identical to one another; however, one of the products of PCR was very similar to the others but was, nonetheless, different. We cloned one of these two genes using the forward primer lcyB-3Rc (5'-AGAAGAGACTTCTTTGGTTGCTC-3' (SEQ ID NO:5) in combination with the 3'-outer primer from the RACE kit. We generated full-length LllcyB cDNA of 1,986 bp by aligning and splicing DNA fragments obtained by 3' and 5'RACE. It contained an open reading frame (ORF) of 1,500 bp, a 5' untranslated region (UTR) of 375 bp and a 3' UTR with a poly(A) tail downstream of the stop codon of 108 bp. Based on homology analyses, we tentatively identified it as a gene for Lcyb (GenBank accession No. GU471230). We succeeded in cloning the second gene, identified later as Llccs (GenBank accession No. JF304153), using the forward primer ccs-3Rc (5'-TCTGGATAAGATGCTCTTCATGGATTGGAG-3' (SEQ ID NO:6) in combination with the 3'-outer primer from the RACE kit. We generated a full-length cDNA sequence of 1,758 bp by aligning and splicing DNA fragments obtained from 3' and 5'RACE. The full-length cDNA included an ORF of 1,425 bp (SEQ ID NO:1), a 5' UTR of 94 bp and a 3' UTR of 239 bp with a poly(A) tail downstream of the termination codon.

The predicted protein was 474 amino acid residues long with a calculated molecular mass of 52.97 kDa and a theoretical pI of 8.4. Amplification of the Llccs gene by PCR, with genomic DNA as a template, yielded a DNA fragment of approximately the same size as the Llccs cDNA. Sequencing of this fragment revealed that Llccs did not include any introns.

Example 2

Expression of the Llccs Transgene in *Iris*

To demonstrate the functionality of the newly cloned Llccs candidate gene, we decided to use it to stably transform nonembryogenic iris (Iris germanica) callus tissue, whose normal yellow color is due to the accumulation of several xanthophylls, such as violaxanthin, the precursor of capsorubin. We performed *Agrobacterium*-mediated transformation with the binary vector pWBVec10a/P35S::Llccs::TNos that harbored Llccs under the control of the Cauliflower mosaic virus (CaMV) 35 S constitutive promoter and the nopaline synthase (Nos) terminator, as described in Jeknic et al. (2012) *Plant Cell Physiol.* 53(11): 1899-1912. Notably, similar results of gene expression in iris can be achieved using biolistic transformation. An example of his transformation using biolistic methods is shown in FIG. 1. General methods of iris transformation have been previously disclosed in our U.S. Pat. No. 6,459,017.

Figure 2:
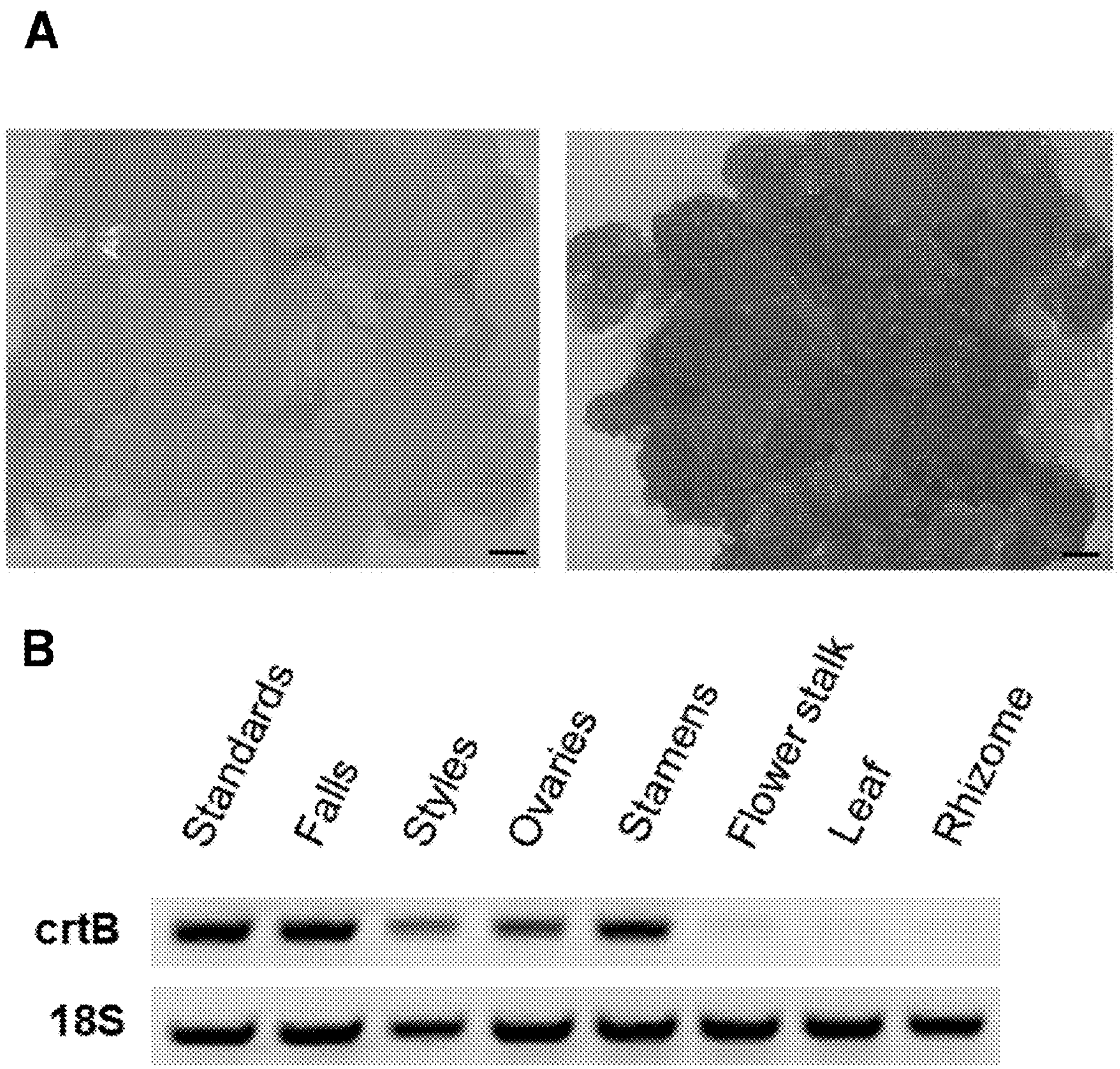
FIG. 2. (A) Wild-type callus tissue of *Iris germanica* 'Hot Property' (left panel) and representative picture of same iris cells transformed and expressing Llccs gene from *Lilium lancifolium* (right panel); bars represent 1 mm. Color versions of these panels are presented in panels (b) and (c), respectively, of FIG. 5 of Jeknic et al. (2012) *Plant & Cell Physiol.* 53(11):1899-1912, where it is shown that wild-type callus of *Iris germanica* 'Hot Property' (left panel) is yellow, while representative picture of same iris cells transformed with and expressing Llccs gene from *Lilium lancifolium* (right panel) are red. (B) Analysis of the expression of the crtB gene under the control of Llccs promoter in different plant parts (standards, falls, styles, ovaries, stamens, flower stalk, leaves and rhizome) of crtB-transgenic *I. germanica* 'Fire Bride' plants. Relative levels of expression of the crtB transgene were normalized with respect to expression of the gene for 18S ribosomal RNA.

The Llccs-expressing transgenic calli changed color from their normal yellow to varying degrees of red to orange in different independent transgenic lines (an example of such a transgenic line is shown in FIG. 2A).

Analysis by HPLC of carotenoids in LLccs-transgenic calli of *Iris germanica* demonstrated the presence of a new carotenoid peak corresponding to authentic capsanthin and its esters. This new peak was not detected in wild-type callus. Analysis of such calli by ultraperformance liquid chromatography-tandem mass spectrometry (UPLC-MS/MS) confirmed the presence of capsanthin, and also revealed the presence of capsorubin.

Details of the chromatographic procedures are reported in Jeknic et al. (2012) *Plant & Cell Physiology* 53(11):1899-1912, the entire contents of which are herein incorporated by reference.

The reported analysis by thin-layer chromatography of carotenoid extracts from leaves of *Nicotiana benthamiana* that had been transfected with an RNA viral vector that harbored the pepper ccs gene revealed the presence of capsanthin; however, no capsorubin was detected even though its precursor, violaxanthin, was observed (Kumagai et al. (1998) *Plant J.* 14:305-315).

Thus, to the best of our knowledge, this is the first time that the in vivo synthesis of capsorubin catalyzed by a heterologous ccs gene has been demonstrated in any plant species. This is also the only example of a stable transformation with a ccs gene whereby the carotenogenic pathway has been successfully re-routed to yield capsanthin and capsorubin.

The appearance of the new pigment(s) in the transgenic callus tissue has demonstrated, for the first time, that Llccs is a functional gene and is responsible for the development of novel red color. Further, we used the TargetP 1.1 software to look for the presence of a transit peptide (TP) sequence in Llccs in an effort to predict the subcellular location of the enzyme. Our results indicated a putative N-terminal pre-sequence that targeted the enzyme to plastids. Development of the red pigment has indicated that the TP had been recognized and processed correctly for targeting L1CCS into chromoplasts.

These results demonstrate that the Llccs gene is capable of functioning properly in iris, catalyzing the synthesis of red pigmentation therein.

Example 3

Identification and Functional Characterization of the Llccs Promoter

Cloning of the Llccs gene allowed us also to clone its upstream regulatory region, namely its promoter region of 1,877 bp (SEQ ID NO:2). After preliminary sequencing, we chose a product of long distance inverse-PCR (LDI-PCR) generated from the BamHI digested sample because it was between 6,000 and 7,000 bp long and was most likely to contain the complete Llccs locus. After sequencing, we designed a pair of primers (L-Llccs-F, 5'-GCAGCAAACCATGAACCTTTG-3' (SEQ ID NO:7), and L-Llccs-R, 5'-ATTAAGATATGTTTCGTGAT-3' (SEQ ID NO:8) for amplification of the Llccs locus that encompassed the promoter region of 1,877 bp upstream of the site of initiation of transcription, the 5' UTR of 94 bp, the Llccs ORF of 1,425 bp and the 3' UTR of 425 bp with a poly(A) tail and a predicted poly(A) signal downstream of the termination codon (GenBank accession No. GU443955).

Further, we have investigated expression patterns of the Llccs promoter. To this end, we have created transgenic *I. germanica* cv. 'Fire Bride' plants, carrying phytoene synthase gene (crtB) under control of the Llccs promoter (PLlccs). Expression patterns of crtB have been analyzed using RT-PCR. Total RNA was isolated from different parts [standards (petals), falls (sepals), stigmas, ovaries, stamens, flower stalk, leaves and rhizome] of control and crtB-transgenic plants using RNeasy Plant Mini Kit (Qiagen Inc., Valencia, Calif.) following the manufacturer's instructions. The concentration and purity of RNA was determined by measuring the absorbance at 260 nm (A260) and 280 nm (A280) with Nanodrop 1000 (Thermo Fisher Scientific, Wilmington, Del.). The RNA samples were then treated with DNase I (Promega, Madison, Wis.) following the manufacturer's instructions, and cleaned using RNeasy Plant Mini Kit, following the RNA cleanup protocol. The final RNA concentration was determined as described above. For RT-PCR analysis, 1 μg of total RNA was used as a template for first-strand cDNA synthesis with Omniscript® Reverse Transcription kit (Qiagen Inc., Valencia, Calif.).). The primers used for RT-PCR analysis of crtB (E-crtB-F, 5'-TCTGATGATGGCCAGGGTGA-3' (SEQ ID NO:9), and E-crtB-R, 5'-TAAACGGGACGCTGCCAAAG-3' (SEQ ID NO:10), and the gene for 18S rRNA (E-185-F, 5'-TAGGTGAACCTGCGGAAGGATCATT-3' (SEQ ID NO:11), and E-18S-R, 5'-CAACTTGCGTTCAAAGACTCGATG-3' (SEQ ID NO:12). PCR amplification was carried out under the following conditions: initial denaturation at 95° C./3 min, followed by 33 cycles of three-step PCR (95° C./30 s, 60° C./30 s, 72° C./1 min) and a final extension at 72° C./7 min using GoTaq® Hot Start Polymerase (0.625 units) with Green GoTaq® Flexi Buffer.

Our results have demonstrated that PLlccs driven crtB was expressed primarily in flowers (standards, falls, styles, ovaries and stamens), with only traces of transcripts detected in leaves and rhizome (FIG. 2B).

In conclusion, the results presented herein demonstrate that we have successfully cloned the gene for capsanthin-capsorubin synthase (Llccs) from tiger lily (*L. lancifolium*). This gene is expressed only in floral tissues, and not in leaves. The data presented herein demonstrate that Llccs is capable of catalyzing the synthesis of both capsanthin and capsorubin in vivo.

As noted above, this is the first time that a heterologous ccs gene has been successfully employed in any plant species to catalyze the in vivo synthesis of capsorubin, and the only example whereby the carotenoid pathway of plants has been successfully re-routed to yield capsanthin and capsorubin via stable transformation with a ccs gene.

Further details of this work are reported in Jeknic et al. (2012) *Plant & Cell Physiology* 53(11):1899-1912, the entire contents of which are herein incorporated by reference.

Embodiments of the invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Nucleotide Sequences

SEQ ID NO: 1: Lilium lancifolium capsanthin-capsorubin synthase (Llccs) nucleotide sequence

ATGTCAACTCTTCAGTTGCCGGCGTTACTCACCGCCGGCGAACTCCGCCACCCTTCAAGGCG

AACAAAGTGCAGTTCTCTCCGTAGCTTTCTAGATCTCACCCCAGTCTCCAAGCCCGAGCCTC

TCACCATCGACATCCCATACCATGACCCCTCCTCCGCCCACCGCTACGATGCCGCCATCATC

GGCTGCGGCCCCGCCGGCCTCCGCCTCGCCGAATGCGCCGCGGCCCGTGGGCTCCGCGTCTG

CTGCATCGACCCCGCCCCCCTCTCCCCCTGGCCCAACAACTACGGCGCCTGGCTCGACGAGC

TCCACCCCCTCGGCCTCGCCTCCATCTTCGACCACATCTGGCCCACCGCCACGATCGCCATC

GACGGCGACAACATCAAGCACCTCTCACGCCCCTACGGCCGCGTCAACCGCAGTTCTCTCAA

AACTCTATTACTAGAAAACTGTACCACCACCGGAGTCAGATTCCACCCCTCCAAAGCCTGGA

ACATCGAGCACGAGGAGCTCCGCTCCTCCGTCTCCTGCTCCGACGGCAGCGCCGTCACCGCC

AGCCTCGTCATCGACGCTGGCGGCTTCAGCACCCCCTTCATCGAGTACGACAGACCGAGAAA

CCGCCGCGGGTACCAGATCGCCCACGGCATCCTCGCCGAGGTCAACCGCCACCCGTTCGACC

TCAACCAGATGCTGCTCATGGACTGGAGCGACGCCCACCTCGACAACGAGCCGCATCTCCGT

GCTCACAACGCTGCTATTCCAACTTTTCTATATGCAATGCCATTCAACGAAAATCTAGTTTT

CCTCGAGGAGACCTCGCTGGTGGGCCGGCCGGTGCTGGACTACAGTGAGGTGAAGAAGAGAA

TGGTGGCGAGGCTGCGACATTTGGGGATTAAGGTGGAGCGGGTGCTGGAGGAGGAGAAGTGT

TTGTTTCCAATGGGAGGTCCGCTGCCGCGGATGCCGCAGAGGGTGATGGGGTATGGCGGGGC

AGGCGGGATGGTGCATCCGTCGTCCGGGTACCAGATTGCTCGGGCGCTGGCGCTCGCGCCGG

AGTTGGCAGAGGCTATGGTGGAGTGTTTGGGATCGACGAGGATGATAACGGGGAAATCGATG

AATTGTAAAGTGTGGGGGAGTTTGTGGCCGGCGGGGAGGAGGTGGGAGAGGGAGTATTACTG

TTTTGGGATGGAGACATTGTTGAGTCTCGATTTGAAGCAGACGAGGAGGTTCTTTGATGCGT

TTTTCAATCTGGAACCGAGGTATTGGCATGGGTTTATGTCGTCGAGGCTGTCGATTACGGAG

CTGGCGCAGCTGAGTTTGTCACTGTTTGCTCATGCGTCTTGGAAGAGTAGGGTGGATGTTGT

GACCAAGTGCCCTTTGCCTTTGGCCAGGATGATTGGCAATCTTGCCTTACAAGCGATTTAG

SEQ ID NO: 2: Lilium lancifolium Llccs promoter nucleotide sequence

GCAGCAAACCATGAACCTTTGTGTTGTACATATATTTATAACCAATTCTCAGTAACTTACTT

GATTATCGAAATCAGCTTCACTGTAACTTCCACTGTTCAGTTTGAGTCTATATATATTTATA

ACCAATTCTCAGTAACTTACTTGATTATCGAAATCAGCTTCACTGTAACTTCCACTGTTCAG

TTTGAGTCTATATGTTCTTTAGCCGTGGCACCTGTTACCAAAACGGGTGCATGTTCATGTAG

CTCAAGACTCACTTTGGGTTAATTCGACTTACCTCCCTTTATTTTAGTTCTGTTGTCTTATA

TTCTGTAGTTTTCGTTGCTTGTCTGGCCTGATTGGTTGATTGTGAAGTAAATTCTTTAGAAT

GAAGCCATAATGGTAGAAAAGTTGTAATACAAAACTAAGAAAAAGAAAAATTAAAAATATTA

ATTATATCTGTTGAGTTTAGTCCCACATCGGTTAGTCTAACCTTACAATCTAAATATAAATA

TGTTATGGGGATACGTTGGATGCTCCGGTTTTTTAAAATGATATCTTGGCAGGTTTGGTTTT

ATGTTGGATGTTCCGGTATTTTAACGTGACATCTTGGCATGTTATCTTTGGCCCAGATGTGT

CACACGTAAGTCACCTTACACCAGATGTGTCACACATAAGTGACCTTATTCCTAACACAGTG

TGTCACACATAAGTCACCTTATTCTCCACCTAATGTATCACACATAAGTGACCTTACAAATT

GACTATGCGGTACCTCTACTACAAGACATTAAAAAGCAAGTCACTATCTTACAAAATAGCAA

TGCCCGTCTTTCCTTTCCTTTCCTTACTTTAATAAAGAAAGACATATATTAATGTCTTTGAT

-continued

TCTCTCGGACTCCTCGATTCAATTAGATTTAATTGAGGGTTTGGTATGAGTTTTACGTCCGC

CTTTTTACATGGGAACAGAACATGTTTTATTTTCCAAGAATGTATCCTAATTTTGGGCCTAA

TTCTACCTTCTCCTCGATTCAATTAGATTTAATTGAGGGTTCGGTATGAGCTCTACGCCCTC

CTTTTTACATGGGAACAAAATGACATGTTTTATTTTCCAAGAATGTATCCTAATTTTGGGCC

TAATTCAACCTTTGATACTCGATTCAACTTCTGATAAAAAATCTTATAAAGACAAAGACCTT

GTGGCTTTCCTTTTATACCAGTGCGGGTGGGTTTGTTGGTCTAAAGCGACATTTAACCCAAC

GGTTTTCTAATCAGTGTGTGTTAGTGGTCTCATGTTCTTTTTCTATGATAGTAGATCCCGCG

GTAGCAAGAAAAAAAAGATTGAGTTCATGCATCAAAACTAATTTATTTTAATACCAACCCGG

AACAAGGGGAGTTTATGCGTGATGGAGGACATAGCTTACAATCATCGGATTTGTTCATGTCA

CTATGCATTTGATTAAGACATTGCACAATGATCCGAACTATCATGCTTACGCCGCCGACACT

TAGAGGCCTCTCATACTATATTTCTTTATTCGAAAGAAAGCTACACAACAATGTTGCCTGAC

ATTAGGCTTAAGTTTGGTGGCCAAACTCTTTTGGCCACCACAACACAACAATGTTGCCTAAT

ATTAGGCTGAATTGTGGCCAAACTCTTTTGGCCACCACAACACAACAATGTTGCCTAATGTT

GTTGCCTGACATTAGGCATGATTTGTGGCCAAACTCTTTTATCGTGAATTTGTGTTATACTC

CCCGCCACGCATCAACATGTCATGTTTTTGTATTCGACATGTCATGTTTTAATCATGTGCTT

CTGTATTCGAATGAACTAAAGGGCAATATGCAATTCCAAGATACCAGACTATAAATTCCCCC

TTTTCAGTGAGCATCAT

SEQ ID NO: 3

TGGAGTTTGGGTTGATGAGT

SEQ ID NO: 4

TGGGAATCTCTCCAATCCAT

SEQ ID NO: 5

AGAAGAGACTTCTTTGGTTGCTC

SEQ ID NO: 6

TCTGGATAAGATGCTCTTCATGGATTGGAG

SEQ ID NO: 7

GCAGCAAACCATGAACCTTTG

SEQ ID NO: 8

ATTAAGATATGTTTCGTGAT

SEQ ID NO: 9

TCTGATGATGGCCAGGGTGA

SEQ ID NO: 10

TAAACGGGACGCTGCCAAAG

SEQ ID NO: 11

TAGGTGAACCTGCGGAAGGATCATT

SEQ ID NO: 12

CAACTTGCGTTCAAAGACTCGATG

What is claimed is:

1. An iris cell transformed with, and which expresses, a nucleotide sequence encoding a capsanthin-capsorubin synthase (ccs) from *Lilium lancifolium.*

2. The iris cell of claim 1, wherein said nucleotide sequence encoding said capsanthin-capsorubin synthase (ccs) comprises the nucleotide sequence shown in SEQ ID NO:1.

3. A transgenic iris plant, comprising said cell of claim 1.

4. The transgenic iris plant of claim 3, wherein said iris plant is cultivar or variety 'Hot Property', 'Dance Man', 'Asian Treasure', 'Strike it Rich', 'Harvest of Memories', 'Early Girl', 'Kissed by the Sun', 'It's Magic', 'Acapulco Gold', 'City of Gold', 'Just a Kiss Away', 'King of Light', 'Dance Till Dawn', or 'Done Me Wrong'.

5. A plant, other than *Lilium lancifolium*, cells of which comprise SEQ ID NO:2 in its genome.

6. The plant of claim 5, wherein said SEQ ID NO:2 is operably linked for expression to a nucleotide sequence encoding a peptide, polypeptide, or protein.

7. The iris cell of claim 1, which is a bearded iris cell.

8. The transgenic iris plant of claim 3, which is a bearded transgenic iris plant.

9. The transgenic iris plant of claim 3, which is an *Iris germanica* or *Iris hollandica* iris plant.

* * * * *

SEQUENCE LISTING

<160> NUMBER OF SEQ ID NOS: 12

<210> SEQ ID NO 1
<211> LENGTH: 1425
<212> TYPE: DNA
<213> ORGANISM: Lilium lancifolium

<400> SEQUENCE: 1
atgtcaactc ttcagttgcc ggcgttactc accgccggcg aactccgcca cccttcaagg 60

-continued

```
cgaacaaagt gcagttctct ccgtagcttt ctagatctca ccccagtctc caagcccgag    120

cctctcacca tcgacatccc ataccatgac ccctcctccg cccaccgcta cgatgccgcc    180

atcatcggct gcggccccgc cggcctccgc ctcgccgaat gcgccgcggc ccgtgggctc    240

cgcgtctgct gcatcgaccc cgcccccctc tccccctggc ccaacaacta cggcgcctgg    300

ctcgacgagc tccacccccct cggcctcgcc tccatcttcg accacatctg gcccaccgcc    360

acgatcgcca tcgacggcga caacatcaag cacctctcac gcccctacgg ccgcgtcaac    420

cgcagttctc tcaaaactct attactagaa aactgtacca ccaccggagt cagattccac    480

ccctccaaag cctggaacat cgagcacgag gagctccgct cctccgtctc ctgctccgac    540

ggcagcgccg tcaccgccag cctcgtcatc gacgctggcg gcttcagcac cccccttcatc   600

gagtacgaca gaccgagaaa ccgccgcggg taccagatcg cccacggcat cctcgccgag    660

gtcaaccgcc acccgttcga cctcaaccag atgctgctca tggactggag cgacgcccac    720

ctcgacaacg agccgcatct ccgtgctcac aacgctgcta ttccaacttt tctatatgca    780

atgccattca acgaaaatct agttttcctc gaggagacct cgctggtggg ccggccggtg    840

ctggactaca gtgaggtgaa gaagagaatg gtggcgaggc tgcgacattt ggggattaag    900

gtggagcggg tgctggagga ggagaagtgt ttgtttccaa tgggaggtcc gctgccgcgg    960

atgccgcaga gggtgatggg gtatggcggg gcaggcggga tggtgcatcc gtcgtccggg   1020

taccagattg ctcgggcgct ggcgctcgcg ccggagttgg cagaggctat ggtggagtgt   1080

ttgggatcga cgaggatgat aacggggaaa tcgatgaatt gtaaagtgtg ggggagtttg   1140

tggccggcgg ggaggaggtg ggagagggag tattactgtt ttgggatgga gacattgttg   1200

agtctcgatt tgaagcagac gaggaggttc tttgatgcgt tttcaatct ggaaccgagg    1260

tattggcatg ggtttatgtc gtcgaggctg tcgattacgg agctggcgca gctgagtttg   1320

tcactgtttg ctcatgcgtc ttggaagagt agggtggatg ttgtgaccaa gtgccctttg   1380

cctttggcca ggatgattgg caatcttgcc ttacaagcga tttag                   1425
```

<210> SEQ ID NO 2
<211> LENGTH: 1877
<212> TYPE: DNA
<213> ORGANISM: Lilium lancifolium

<400> SEQUENCE: 2

```
gcagcaaacc atgaaccttt gtgttgtaca tatatttata accaattctc agtaacttac     60

ttgattatcg aaatcagctt cactgtaact tccactgttc agtttgagtc tatatatatt    120

tataaccaat tctcagtaac ttacttgatt atcgaaatca gcttcactgt aacttccact    180

gttcagtttg agtctatatg ttctttagcc gtggcacctg ttaccaaaac gggtgcatgt    240

tcatgtagct caagactcac tttgggttaa ttcgacttac ctccctttat tttagttctg    300

ttgtcttata ttctgtagtt ttcgttgctt gtctggcctg attggttgat tgtgaagtaa    360

attctttaga atgaagccat aatggtagaa aagttgtaat acaaaactaa gaaaaagaaa    420

aattaaaaat attaattata tctgttgagt ttagtcccac atcggttagt ctaaccttac    480

aatctaaata taaatatgtt atggggatac gttggatgct ccggtttttt aaaatgatat    540

cttggcaggt ttggttttat gttggatgtt ccggtatttt aacgtgacat cttggcatgt    600

tatctttggc ccagatgtgt cacacgtaag tcaccttaca ccagatgtgt cacacataag    660

tgaccttatt cctaacacag tgtgtcacac ataagtcacc ttattctcca cctaatgtat    720

cacacataag tgaccttaca aattgactat gcggtacctc tactacaaga cattaaaaag    780
```

-continued caagtcacta tcttacaaaa tagcaatgcc cgtctttcct ttcctttcct tactttaata 840
aagaaagaca tatattaatg tctttgattc tctcggactc ctcgattcaa ttagatttaa 900
ttgagggttt ggtatgagtt ttacgtccgc ctttttacat gggaacagaa catgttttat 960
tttccaagaa tgtatcctaa ttttgggcct aattctacct tctcctcgat tcaattagat 1020
ttaattgagg gttcggtatg agctctacgc cctccttttt acatgggaac aaaatgacat 1080
gttttatttt ccaagaatgt atcctaattt tgggcctaat tcaacctttg atactcgatt 1140
caacttctga taaaaaatct tataaagaca aagaccttgt ggctttcctt ttataccagt 1200
gcgggtgggt ttgttggtct aaagcgacat ttaacccaac ggttttctaa tcagtgtgtg 1260
ttagtggtct catgttcttt ttctatgata gtagatcccg cggtagcaag aaaaaaaaga 1320
ttgagttcat gcatcaaaac taatttattt taataccaac ccggaacaag gggagtttat 1380
gcgtgatgga ggacatagct tacaatcatc ggatttgttc atgtcactat gcatttgatt 1440
aagacattgc acaatgatcc gaactatcat gcttacgccg ccgacactta gaggcctctc 1500
atactatatt tctttattcg aaagaaagct acacaacaat gttgcctgac attaggctta 1560
agtttggtgg ccaaactctt ttggccacca caacacaaca atgttgccta atattaggct 1620
gaattgtggc caaactcttt tggccaccac aacacaacaa tgttgcctaa tgttgttgcc 1680
tgacattagg catgatttgt ggccaaactc ttttatcgtg aatttgtgtt atactccccg 1740
ccacgcatca acatgtcatg tttttgtatt cgacatgtca tgttttaatc atgtgcttct 1800
gtattcgaat gaactaaagg gcaatatgca attccaagat accagactat aaattccccc 1860
ttttcagtga gcatcat 1877

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
tggagtttgg gttgatgagt 20

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
tgggaatctc tccaatccat 20

<210> SEQ ID NO 5
<211> LENGTH: 23
<212> TYPE: DNA
<213> ORGANISM: Artificial Sequence
<220> FEATURE:
<223> OTHER INFORMATION: PCR primer

<400> SEQUENCE: 5
agaagagact tctttggttg ctc 23

<210> SEQ ID NO 6
<211> LENGTH: 30
<212> TYPE: DNA

<213> ORGANISM: Artificial Sequence
<220> FEATURE:
<223> OTHER INFORMATION: PCR primer

<400> SEQUENCE: 6
tctggataag atgctcttca tggattggag 30

<210> SEQ ID NO 7
<211> LENGTH: 21
<212> TYPE: DNA
<213> ORGANISM: Artificial Sequence
<220> FEATURE:
<223> OTHER INFORMATION: PCR primer

<400> SEQUENCE: 7
gcagcaaacc atgaaccttt g 21

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
attaagatat gtttcgtgat 20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
tctgatgatg gccagggtga 20

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
taaacgggac gctgccaaag 20

<210> SEQ ID NO 11
<211> LENGTH: 25
<212> TYPE: DNA
<213> ORGANISM: Artificial Sequence
<220> FEATURE:
<223> OTHER INFORMATION: PCR primer

<400> SEQUENCE: 11
taggtgaacc tgcggaagga tcatt 25

<210> SEQ ID NO 12
<211> LENGTH: 24
<212> TYPE: DNA
<213> ORGANISM: Artificial Sequence -continued

```
<220> FEATURE:
<223> OTHER INFORMATION: PCR primer

<400> SEQUENCE: 12

caacttgcgt tcaaagactc gatg                                          24
```